US010801831B2

(12) United States Patent
Aizawa et al.

(10) Patent No.: US 10,801,831 B2
(45) Date of Patent: Oct. 13, 2020

(54) SPECKLE MEASUREMENT APPARATUS AND SPECKLE MEASUREMENT METHOD (71) Applicant: SONY CORPORATION, Tokyo (JP)

(72) Inventors: Kota Aizawa, Tokyo (JP); Atsushi Okubo, Tokyo (JP); Yoshihiro Wakita, Tokyo (JP)

(73) Assignee: SONY CORPORATION, Tokyo (JP)

( * ) Notice: Subject to any disclaimer, the term of this patent is extended or adjusted under 35 U.S.C. 154(b) by 105 days.

(21) Appl. No.: 16/084,450

(22) PCT Filed: Feb. 7, 2017

(86) PCT No.: PCT/JP2017/004344
§ 371 (c)(1),
(2) Date: Sep. 12, 2018

(87) PCT Pub. No.: WO2017/175470
PCT Pub. Date: Oct. 12, 2017

(65) Prior Publication Data
US 2019/0094009 A1 Mar. 28, 2019

(30) Foreign Application Priority Data
Apr. 5, 2016 (JP) .................... 2016-075759

(51) Int. Cl.
G01B 9/02 (2006.01)
A61B 5/00 (2006.01)
(Continued)

(52) U.S. Cl.
CPC ........ *G01B 9/02094* (2013.01); *A61B 5/0033* (2013.01); *A61B 5/0059* (2013.01);
(Continued)

(58) Field of Classification Search
CPC ....... A61B 5/0059; A61B 5/021; A61B 5/033; G01B 9/02091; G01B 9/02004; G01B 9/02083; G01B 9/02002; G01B 9/02044
See application file for complete search history.

(56) References Cited

U.S. PATENT DOCUMENTS 7,382,949 B2 * 6/2008 Bouma .............. A61B 1/00183
385/25
8,638,991 B2 1/2014 Zalevsky et al.
(Continued)

FOREIGN PATENT DOCUMENTS

JP H02-268725 A 11/1990
JP H10-290791 A 11/1998
(Continued)

OTHER PUBLICATIONS

Qui et al., "Spatiotemporal laser speckle contrast analysis for blood flow imaging with maximized speckle contrast", (2010), Journal of Biomedical Optics, vol. 15(1), pp. 016003-1 to 016003-5. (Year: 2010).*

*Primary Examiner* — Diane D Mizrahi
(74) *Attorney, Agent, or Firm* — Paratus Law Group, PLLC (57) ABSTRACT There is provided a speckle measurement apparatus to improve accuracy of flow velocity measurement or the like of particulates such as erythrocytes, the speckle measurement apparatus including an imager that captures scattered light images returned from an object to be measured when the object to be measured is irradiated with coherent light as speckle images, and a controller that determines a measurement area that is the same site of the object to be measured in a plurality of the speckle images captured continuously in time series by the imager by incorporating a displacement
(Continued)

amount of a relative positional relationship between the object to be measured and the imager.

5 Claims, 4 Drawing Sheets (51) Int. Cl.
*A61B 5/026* (2006.01)
*G01P 5/26* (2006.01)
*G06T 7/246* (2017.01)
*A61B 5/1455* (2006.01)
*G01P 5/22* (2006.01)
*A61B 5/021* (2006.01)
*A61B 5/024* (2006.01)

(52) U.S. Cl.
CPC .............. *A61B 5/021* (2013.01); *A61B 5/024* (2013.01); *A61B 5/0261* (2013.01); *A61B 5/14551* (2013.01); *G01B 9/02083* (2013.01); *G01P 5/22* (2013.01); *G01P 5/26* (2013.01); *G06T 7/246* (2017.01); *G06T 2207/30104* (2013.01)

(56) References Cited

U.S. PATENT DOCUMENTS

| | | | |
|---|---|---|---|
| 2011/0013002 A1* | 1/2011 | Thompson | A61B 5/0059 348/77 |
| 2014/0357990 A1 | 12/2014 | Wang | |
| 2017/0188853 A1* | 7/2017 | Nakao | A61B 5/0066 |

FOREIGN PATENT DOCUMENTS

| | | |
|---|---|---|
| JP | 2003-164431 A | 6/2003 |
| JP | 2010-508056 A | 3/2010 |
| JP | 2014-500751 A | 1/2014 |
| JP | 2015-527096 A | 9/2015 |
| WO | WO 2010/096453 A1 | 8/2010 |
| WO | WO 2012/096878 A2 | 7/2012 |
| WO | WO 2013/049123 A1 | 4/2013 |

* cited by examiner

Speckle image at time t0

SPECKLE MEASUREMENT APPARATUS AND SPECKLE MEASUREMENT METHOD

CROSS REFERENCE TO PRIOR APPLICATION

This application is a National Stage Patent Application of PCT International Patent Application No. PCT/JP2017/004344 (filed on Feb. 7, 2017) under 35 U.S.C. § 371, which claims priority to Japanese Patent Application No. 2016-075759 (filed on Apr. 5, 2016), which are all hereby incorporated by reference in their entirety.

TECHNICAL FIELD

The present technology relates to a speckle measurement apparatus and a speckle measurement method.

BACKGROUND ART

In a case where an object having an uneven structure is irradiated with coherent light such as laser light and scattered light reflected from the object is observed by an imager, a granular pattern called as a speckle pattern appears. In a case where a non-moving object is irradiated with laser light, the speckle pattern is not changed and light intensity is also not changed. In a case where a moving object is irradiated with laser light, the speckle pattern is changed depending on the velocity of the moving object. According to this principle, if a time change of speckle intensity is determined, the velocity, the size, or the like of moving particles can be determined. This principle is applied to measure parameters of a living body such as a blood flow velocity of erythrocytes in biometric measurement.

For example, Patent Literature 1 discloses a technique of measuring a time series change at a specific point and estimating a movement parameter of a particle group.

Patent Literature 2 discloses that a speckle image is captured by an imager to measure a vibration phenomenon on a roughened surface.

CITATION LIST

Patent Literature

Patent Literature 1: Translation of PCT International Application Publication No. 2014-500751
Patent Literature 2: U.S. Pat. No. 8,638,991

DISCLOSURE OF INVENTION

Technical Problem

However, in order to practically use the speckle measurement method, for example, for measuring the blood flow velocity of erythrocytes or the like in the biometric measurement as described above, there remain problems to be solved or improved in a variety of points.

The present technology is made in view of the above-mentioned circumstances, and it is an object of the present technology to provide a speckle measurement apparatus and a speckle measurement method capable of improving accuracy of flow velocity measurement or the like of particulates such as erythrocytes.

Solution to Problem

In order to solve the problem, a speckle measurement apparatus according to an embodiment of the present technology includes an imager that captures scattered light images returned from an object to be measured when the object to be measured is irradiated with coherent light as speckle images; and a controller that determines a measurement area that is the same site of the object to be measured in a plurality of the speckle images captured continuously in time series by the imager by incorporating a displacement amount of a relative positional relationship between the object to be measured and the imager.

According to the speckle measurement apparatus of the present technology, in speckle measurement components of a relative movement between the object to be measured and the imager due to a body movement and vibration of the imager are canceled and only speckle components due to a movement of particulates such as erythrocytes can be extracted as the object to be measured. Thus, speckle measurement accuracy can be improved.

The controller may be configured to compare the plurality of speckle images captured continuously in time series by the imager, detect the displacement amount of the relative positional relationship between the object to be measured and the imager, and determine the measurement area that is the same site of the object to be measured in the plurality of speckle images according to the detected displacement amount.

In addition, the controller may be configured to divide a coordinate space of a speckle image captured by the imager into a plurality of divided areas each having a predetermined size, determine the divided area having least area-specific noise components as the measurement area, retrieve an area with a highest coincidence with the speckle image of the measurement area from a speckle image at next time, and regard the retrieved area as the measurement area at the next time.

Further, the controller may be configured to determine an image signal where a speckle response is not linearly changed with respect to a change of a coherent light intensity as the local noise.

Further, the controller may be configured to exclude the divided area where any of an average value, a maximum value, and a median of a contrast difference of brightness of all existing speckles is a threshold value or less from the measurement area.

In addition, a speckle measurement method according to the present technology includes irradiating an object to be measured with coherent light;
capturing scattered light images returned from an object to be measured as speckle images; and
determining by a controller a measurement area that is the same site of the object to be measured in the plurality of speckle images captured continuously in time series by incorporating a displacement amount of a relative positional relationship between the object to be measured and an imager.

Advantageous Effects of Invention

As described above, according to the present technology, accuracy of flow velocity measurement or the like of particulates such as erythrocytes that are moved inside an object generating a fixed speckle pattern such as a skin can be improved.

MODE(S) FOR CARRYING OUT THE INVENTION

Hereinafter, embodiments of the present technology will be described with reference to the drawings.

First Embodiment

[Overview]

Figure 1:
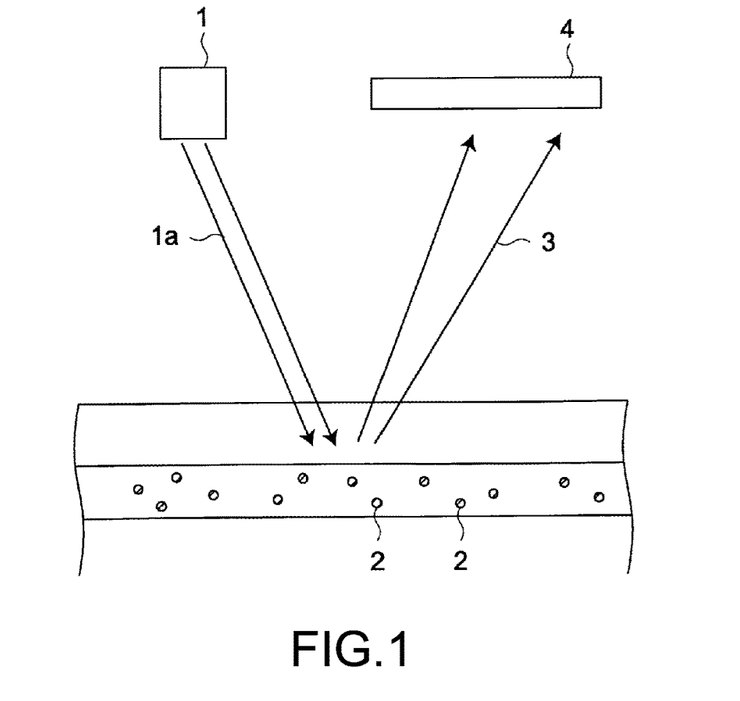
FIG. 1 is a view of illustrating an overview of a speckle measurement apparatus.

The present specification describes a speckle measurement apparatus that irradiates an object to be measured 2 such as erythrocytes flowing through a living body with coherent light 1a such as laser light from a light source 1, captures reflected scattered light 3 by an imager 4, and analyzes speckle images provided by capturing to measure a blood flow velocity, for example, as shown in FIG. 1.

In such a speckle measurement apparatus, in a case where a relative positional relationship between the object to be measured 2 and the imager 4 is changed due to a body movement (including pulsation) and vibration of the imager 4 during measurement, components of the movement are superimposed on the whole speckle images. It is therefore difficult to estimate an accurate flow rate to the object to be measured 2 such as erythrocytes.

An object of the speckle measurement apparatus of the first embodiment according to the present technology is to improve speckle measurement accuracy by removing the components of the movement in the relative positional relationship between the object to be measured 2 and the imager 4 from a speckle measurement result.

In order to achieve the object, the speckle measurement apparatus of the first embodiment includes the imager 4 that captures speckle images of scattered light 3 returned from the object to be measured 2 when the object to be measured 2 is irradiated with coherent light 1a, and an arithmetic processing circuit that is a controller that determines a measurement area that is the same site of the object to be measured 2 in a plurality of the speckle images captured continuously in time series by the imager 4 by incorporating a displacement amount of a relative positional relationship between the object to be measured 2 and the imager 4.

More specifically, the arithmetic processing circuit is configured to compare the plurality of speckle images captured continuously in time series by the imager 4, detect the displacement amount of the relative positional relationship between the object to be measured 2 and the imager 4, and determine the measurement area that is the same site of the object to be measured 2 in the plurality of speckle images according to the detected displacement amount.

In a speckle measurement apparatus of a second embodiment according to the present technology, the arithmetic processing circuit is configured to divide a speckle image captured by the imager 4 into a plurality of divided areas each having a predetermined size, determine the divided area having least area-specific noise components as the measurement area, and retrieve one or a plurality of divided areas with a relatively less coincidence with the speckle image of the measurement area from a speckle image at next time to regard the retrieved area as the measurement area at the next time.

First Embodiment

Hereinafter, a speckle measurement apparatus of a first embodiment according to the present technology will be described in detail.

Figure 2:
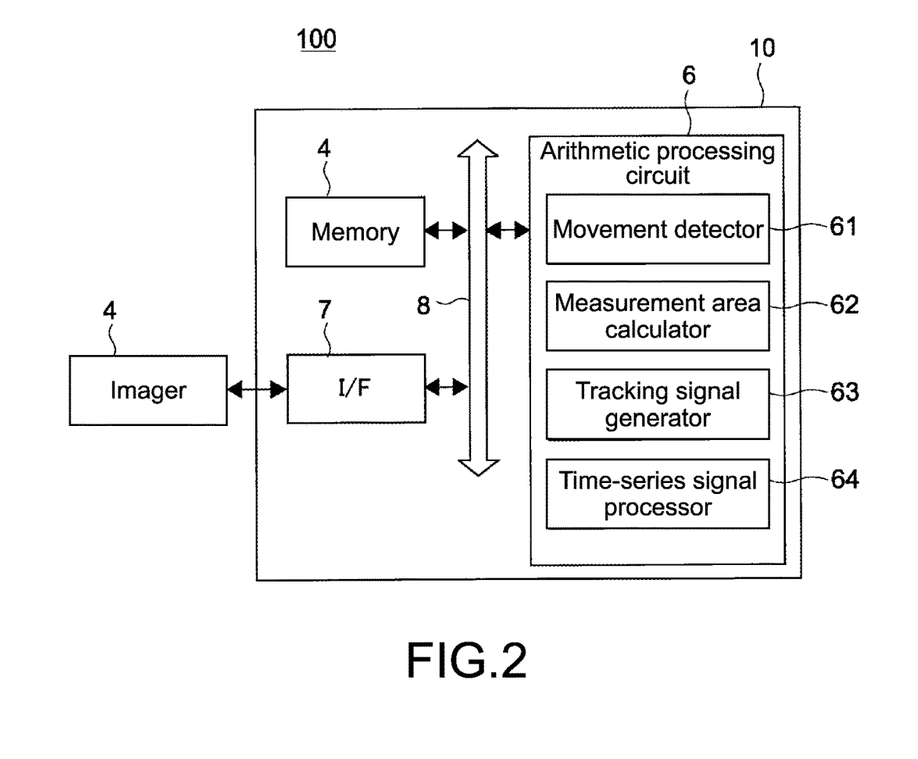
FIG. 2 is a block diagram showing a structure of a speckle measurement apparatus 100 of a first embodiment according to the present technology.

FIG. 2 is a block diagram showing a structure of a speckle measurement apparatus 100 of the first embodiment.

As shown in FIG. 2, the speckle measurement apparatus 100 includes a light source 1 such as laser light source that irradiates the object to be measured 2 with coherent light such as laser light, and a speckle measurement system 10 that generates speckle images by receiving scattered light reflected by the object to be measured 2 and measures, for example, a blood flow velocity of erythrocytes from a plurality of the speckle images provided continuously in time series.

The speckle measurement system 10 includes the imager 4 such as a CCD (Charge Coupled Device) and a CMOS (Complementary Metal Oxide Semiconductor), an arithmetic processing circuit 6, and a memory 7. The arithmetic processing circuit 6 and the memory 7 may be included in one or more computers 5. The imager 4 is connected to a bus 9 via an interface 8.

The computer 5 may be connected to the imager 4 via a network. In addition, a plurality of computers may perform concurrently parallel processing of the speckle measurement.

The arithmetic processing circuit 6 functions as a movement detector 61, a measurement area calculator 62, a tracking signal generator 63, a time-series signal processor 64 or the like according to a program stored in the memory 7 or the like.

The memory 7 stores the plurality of speckle images captured continuously in time series by the imager 4.

The movement detector 61 detects the movement in the relative positional relationship between the object to be measured 2 and the imager 4. More specifically, the movement detector 61 repeatedly displaces the positional relationship between the time-series continued two speckle images stored in the memory 7 for a predetermined unit such as a pixel, matches the two, and calculates the distance between the two at the time of the maximum coincidence as the displacement amount of the relative positional relationship between the object to be measured 2 and the imager 4. Alternatively, in order to further increase the accuracy, the positional relationship between the two speckle images may be displaced each other and matched for a subpixel unit by further dividing the pixel.

The speckle images of coherent light scattered by a fixed structure such as a skin tissue do not have largely changed shapes in the two speckle images continued in time series. Thus, if the movement in the relative positional relationship between the two speckle images continued in time series is known, the measurement area corresponding to the same site of the object to be measured 2 in the two speckle images can be calculated.

According to the displacement amount of the relative positional relationship between the time-series continued two speckle images detected by the movement detector 61, the measurement area calculator 62 calculates where the measurement area set to the speckle image at an initial time from the two speckle images corresponds to the speckle image at the next time. Specifically, in this embodiment, the measurement area, for example, having a predetermined horizontal and vertical size at the center, of the speckle image at the initial time is initially set. In a case where the relative positional relationship between the object to be measured 2 and the light source 1 or the imager 4 is changed due to the body movement and vibration of the imager 4 during the measurement, the measurement area is also changed for the displacement amount. Thus, the measurement area calculator 62 can calculate the measurement area of the speckle image at the next time from the displacement amount detected by the movement detector 61.

The tracking signal generator 63 generates an evaluation value such as an average value of respective pixel values of the measurement area determined by the measurement area calculator 62 as a signal for speckle measurement.

The time-series signal processor 64 processes the signal generated by the tracking signal generator 63 and calculates a velocity, a particle diameter, or the like of particulates such as erythrocytes. For example, the time-series signal processor 64 may measure the velocity of erythrocytes by the Laser Doppler method and estimate the particle diameter by the DLS (dynamic light scattering method).

[Operation]

Next, an operation of the speckle measurement apparatus 100 in this embodiment will be described.

Figure 3:
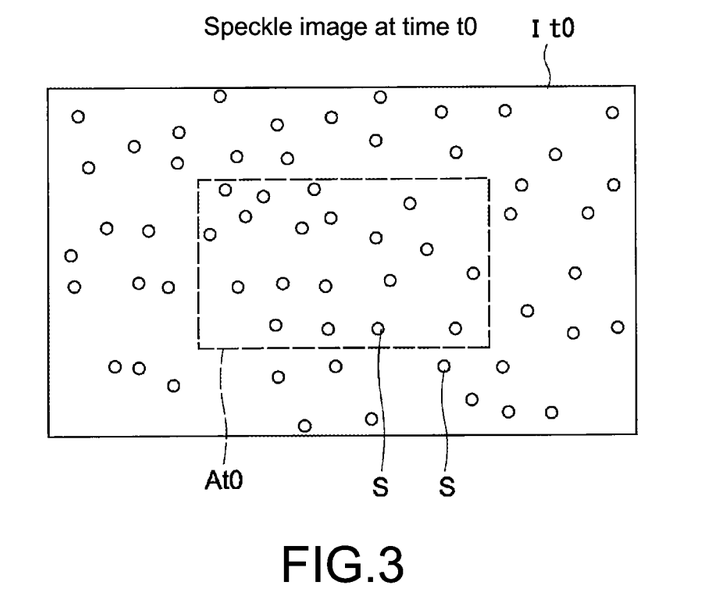
FIG. 3 is a view showing a whole speckle image It0 and a measurement area At0 captured by an imager 4 at a certain time t0 in the speckle measurement apparatus 100 of the first embodiment.

FIG. 3 shows a whole speckle image It0 and a measurement area At0 captured by the imager 4 at a certain time t0.

In this embodiment, an area having a predetermined horizontal and vertical size at the center of a speckle image I is set as an initial measurement area At0 in advance. In a case where a movement direction in the relative positional relationship between the object to be measured 2 and the imager 4 is unknown, the measurement area At0 is preferably arranged at the center of the speckle image in this manner. Note that signs S shown in FIG. 3 represent speckles corresponding to erythrocytes. In fact, one speckle is one spot pattern that repeats blinks as time goes.

Figure 4:
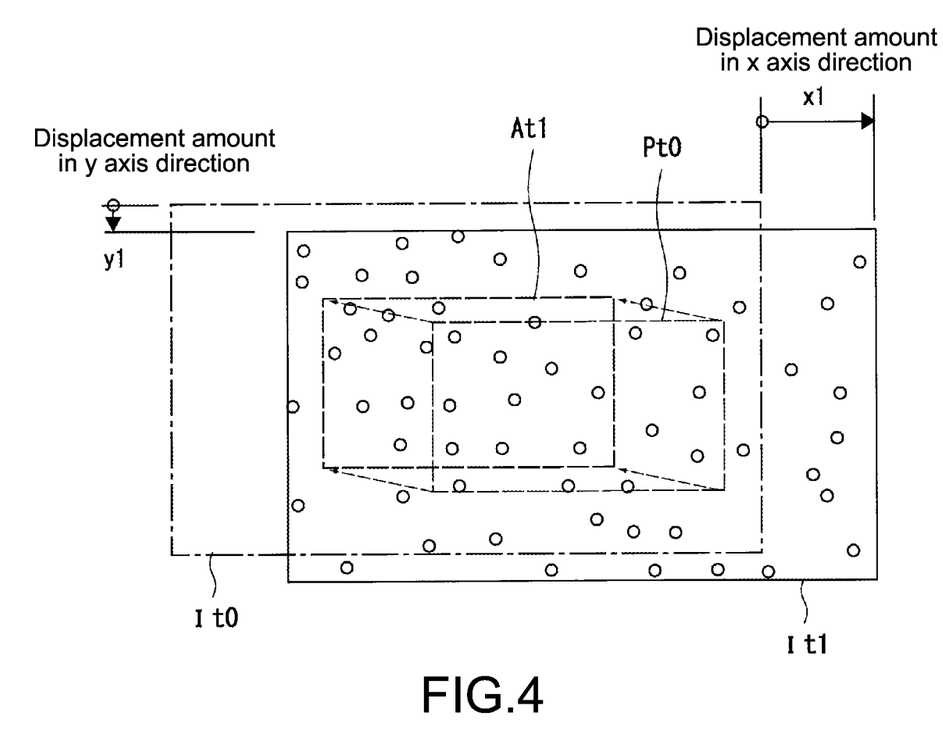
FIG. 4 is a view showing a positional relationship between a whole speckle image It0 captured at the time t0 and the whole speckle image It1 captured at the next time t1 by the imager 4 and a measurement area At1 at the next time t1 calculated according to the positional relationship in the speckle measurement apparatus 100 of the first embodiment.

FIG. 4 shows a positional relationship between the whole speckle image It0 captured at the time t0 and the whole speckle image It1 captured at the next time t1 by the imager 4, and the measurement area At1 at the next time t1 calculated according to the positional relationship.

This example shows a case that the speckle image It0 at the time t0 and the speckle image It1 at the time t1 are repeatedly displaced each other for a pixel unit and matched, and the distance between the two in the x axis direction is x1 and the distance between the two in the y axis direction is y1 at the time of the maximum coincidence.

According to the displacement amount, the measurement area calculator 62 calculates the area of the same site of the object to be measured 2 corresponding to the measurement area At0 at time t0 as the measurement area At1 at time t1 in the speckle image It1 at the time t1. Specifically, the measurement area At1 of the speckle image It1 at time t1 moves from a position Pt0 of the measurement area At0 at the former time t0 within a coordinate space of the speckle images for the displacement amount.

Next, the tracking signal generator 63 generates an evaluation value such as an average value of the respective pixel values of the measurement area at the respective times as a signal for speckle measurement and outputs the signal to the time-series signal processor 64. The time-series signal processor 64 processes the signal for speckle measurement at the respective times and calculates a velocity, a particle diameter, or the like of particulates such as erythrocytes.

As described above, according to the speckle measurement apparatus 100 in this embodiment, the components of the relative movement between the object to be measured 2 and the imager 4 due to the body movement and vibration of the imager 4 are canceled and only speckle components due to the movement of the particulates such as erythrocytes can be extracted. Thus, speckle measurement accuracy can be improved.

Second Embodiment

Hereinafter, a speckle measurement apparatus 100A of a second embodiment according to the present technology will be described in detail.

Figure 5:
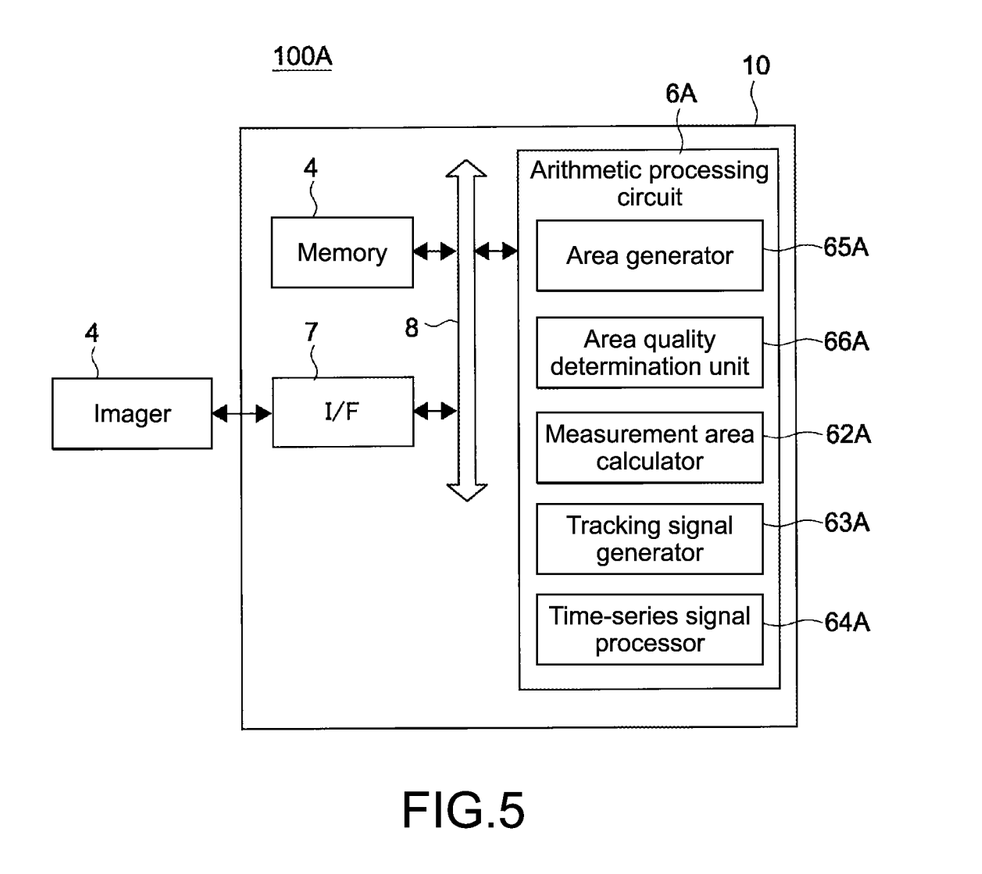
FIG. 5 is a block diagram showing a structure of a speckle measurement apparatus 100A of a second embodiment according to the present technology.

FIG. 5 is a block diagram showing a structure of the speckle measurement apparatus 100A of the second embodiment according to the present technology.

As shown in FIG. 5, in the speckle measurement apparatus 100A, an arithmetic processing circuit 6A includes an area generator 65A, an area quality determination unit 66A, a measurement area calculator 62A, a tracking signal generator 63A, and a time-series signal processor 64A.

The area generator 65A divides whole speckle images captured by the imager 4 into a plurality of divided areas each having a predetermined size. The size of the divided area is set such that at least a plurality of speckle images are present. The positional relationship between the speckle particles of the plurality of particles present in one divided area is not affected by the movement in the relative positional relationship between the object to be measured 2 and the imager 4. Accordingly, it is necessary that the divided area is set to have a size in which a plurality of speckle particles are present in order to distinguish a change of the speckle image due to the movement in the relative positional relationship between the object to be measured 2 and the imager 4 from a change of the speckle image due to the movement of the particles.

The area quality determination unit 66A evaluates the quality as the measurement area of each divided area of the speckle image. For example, various area-specific noise factors including light from outside may present in the site of the object to be measured 2 corresponding to the whole speckle image. Here, the area-specific noise is different from the movement of the overall speckle image caused by the relative movement between the object to be measured 2 and the imager 4 due to the body movement and vibration of the imager 4.

In order to evaluate the quality as the measurement area of each divided area of the speckle image, the area quality determination unit 66A determines an area where a speckle response is not linearly changed with respect to a change of a laser light intensity, an area where an average value or a maximum value of a contrast difference of brightness of all speckles is a threshold value or less, or the like as the area where the area-specific noise is present. In other words, the area quality determination unit 66A determines the divided area having the area-specific noise as low as possible as the high quality measurement area.

The measurement area calculator 62A repeatedly displaces a retrieval window having the same size as the divided area for a predetermined unit, for example, a pixel or the like in the speckle image of the measurement area determined by the area quality determination unit 66A with respect to the speckle image at the next time, and matches the two. The movement detector 61 determines the retrieval window having the maximum coincidence as the measurement area of the speckle image at the next time.

The tracking signal generator 63A calculates, for example, an average value of the respective pixel values of the measurement area determined by the measurement area calculator 62A and outputs it as a signal for speckle measurement.

The time-series signal processor 64A processes the signal generated by the signal generator and calculates a velocity, a particle diameter, or the like of erythrocytes or the like. For example, the time-series signal processor 64A may measure the velocity of erythrocytes by the Laser Doppler method and estimate the particle diameter by the DLS (dynamic light scattering method).

[Operation]

Next, an operation of the speckle measurement apparatus 100A in this embodiment will be described.

Figure 6:
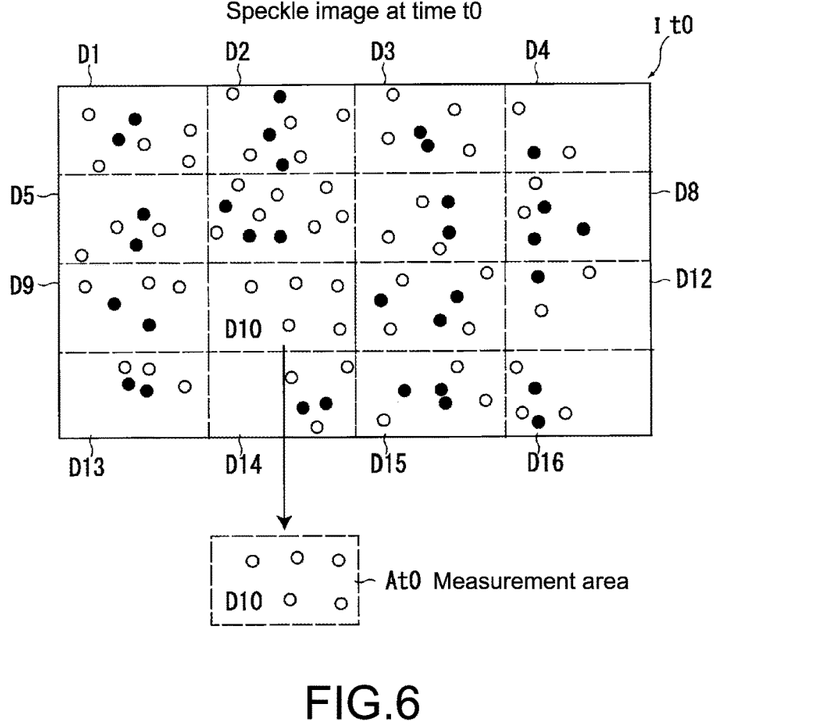
FIG. 6 is a view showing a whole speckle image It0 captured at the time t0 and divided areas D1-D16 set thereto in the speckle measurement apparatus 100A of the second embodiment.

FIG. 6 shows a whole speckle image It0 captured by the imager 4 at a certain time t0 and divided areas D1-D16 set thereto.

In this embodiment, as initial values of the divided areas, 4×4 in horizontal and vertical directions, i.e., a total of 16 areas D1-D16 are set.

In FIG. 6, white circles represent speckles corresponding to erythrocytes and black circles represent speckles by a local noise other than erythrocytes.

The area quality determination unit 66A evaluates the quality of 16 divided areas D1-D16 as the measurement area of the speckle image and determines one or a plurality of divided areas having a high quality as the measurement area. In the embodiment of FIG. 6, the divided area D10 is determined as the divided area having the highest quality and the divided area D10 is determined as the measurement area At0 at the time t0.

Figure 7:
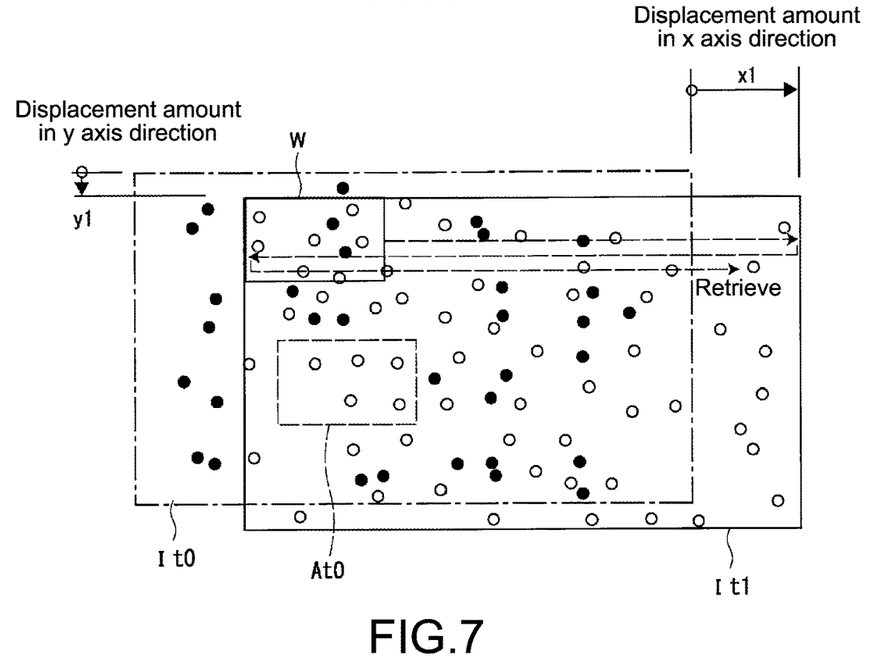
FIG. 7 is a view showing a positional relationship between the whole speckle image It0 captured at the time t0 and a whole speckle image It1 captured at the next time t1 and the measurement area At1 at the next time t1 calculated according to the positional relationship in the speckle measurement apparatus 100A of the second embodiment.

FIG. 7 shows a positional relationship between the whole speckle image It0 captured at the time t0 and the whole speckle image It1 captured at the next time t1 and the measurement area At1 at the next time t1 calculated according to the positional relationship.

In this example, the measurement area calculator 62A repeatedly displaces a retrieval window W having the same size as one divided area for a predetermined unit such as a pixel in the speckle image at the next time t1 with respect to the speckle image of the measurement area At0 at the time t0, and matches the two. The measurement area calculator 62A determines the area of the retrieval window W at the time of the maximum coincidence as the measurement area At1 at the next time t1.

Thus, a high quality measurement area A that is the same site of the object to be measured 2 and has less noise components can be calculated in the two speckle images captured continuously in time series by the imager 4.

Next, the tracking signal generator 63A generates a signal for speckle measurement from the respective pixel values of the measurement area at the respective times and outputs the signal to the time-series signal processor 64A. The time-series signal processor 64 processes the signal for speckle measurement at the respective times and calculates a velocity, a particle diameter, or the like of particulates such as erythrocytes.

In a case where the area quality determination unit 66A outputs the plurality of areas, the above-described processing is executed for the number of areas and the measurement area is calculated. For example, by averaging numerical values such as the velocity and the particle diameter calculated from the plurality of areas, the speckle measurement with higher accuracy is possible.

As described above, also according to the speckle measurement apparatus 100A in this embodiment, the components of the relative movement between the object to be measured 2 and the imager 4 due to the body movement and vibration of the imager 4 are canceled and only speckle components due to the movement of the particulates such as erythrocytes can be extracted. Thus, speckle measurement accuracy can be improved. In addition, since the measurement area having less local noise components is selected, accuracy can be further improved.

[Modified]

In the above-described embodiments, there are described the speckle measurement apparatuses 100 and 100A each of which irradiates the object to be measured 2 with laser light and directly captures the scattered light image returned from the object to be measured 2 by the imager 4. Also, the present disclosure is applicable to the speckle measurement apparatus 100A which captures the scattered light image returned from the object to be measured 2 by the imager 4 via a lens.

With this structure, the images of the object to be measured 2 are obtained. By comparing the two images of objects to be measured 2 continuously captured, the movement in the relative positional relationship between the object to be measured 2 and the imager 4 can be detected.

The present technology may also have the following structures.

(1)

A speckle measurement apparatus, including:

an imager that captures scattered light images returned from an object to be measured when the object to be measured is irradiated with coherent light as speckle images; and a controller that determines a measurement area that is the same site of the object to be measured in a plurality of the speckle images captured continuously in time series by the imager by incorporating a displacement amount of a relative positional relationship between the object to be measured and the imager.

(2)

The speckle measurement apparatus according to (1) above, in which the controller is configured to compare the plurality of speckle images captured continuously in time series by the imager, detect the displacement amount of the relative positional relationship between the object to be measured and the imager, and determine the measurement area that is the same site of the object to be measured in the plurality of speckle images according to the detected displacement amount.

(3)

The speckle measurement apparatus according to (1) above, in which the controller is configured to divide a coordinate space of a speckle image captured by the imager into a plurality of divided areas each having a predetermined size, determine the divided area having least area-specific noise components as the measurement area, retrieve an area with a highest coincidence with the speckle image of the measurement area from a speckle image at next time, and regard the retrieved area as the measurement area at the next time.

(4)

The speckle measurement apparatus according to (3) above, in which the controller is configured to determine an image signal that is not linearly changed with respect to a change of a coherent light intensity as a local noise.

(5)

The speckle measurement apparatus according to (3) or (4) above, in which the controller is configured to exclude the divided area where any of an average value, a maximum value, and a median of a contrast difference of brightness of all existing speckles is a threshold value or less from the measurement area.

(6)

A speckle measurement method, including:

irradiating an object to be measured with coherent light;

capturing scattered light images returned from the object to be measured as speckle images; and determining by a controller a measurement area that is the same site of the object to be measured in a plurality of the speckle images captured continuously in time series by incorporating a displacement amount of a relative positional relationship between the object to be measured and an imager.

(7)

The speckle measurement method according to (1) above, in which the controller compares the plurality of speckle images captured continuously in time series by the imager, detects the displacement amount of the relative positional relationship between the object to be measured and the imager, and determines the measurement area that is the same site of the object to be measured in the plurality of speckle images according to the detected displacement amount.

(8)

The speckle measurement method according to (7) above, in which the controller divides a coordinate space of a speckle image captured by the imager into a plurality of divided areas each having a predetermined size, determines the divided area having least area-specific noise components as the measurement area, retrieves an area with a highest coincidence with the speckle image of the measurement area from a speckle image at next time, and regards the retrieved area as the measurement area at the next time.

(9)

The speckle measurement method according to (8) above, in which the controller determines an image signal that is not linearly changed with respect to a change of a coherent light intensity as the local noise.

(10)

The speckle measurement method according to (8) or (9) above, in which the controller excludes the divided area where any of an average value, a maximum value, and a median of a contrast difference of brightness of all existing speckles is a threshold value or less from the measurement area.

REFERENCE SIGNS LIST 1 light source
2 object to be measured
4 imager
6 arithmetic processing circuit
7 memory
10 speckle measurement system
61 movement detector
62, 62A measurement area calculator
63, 63A tracking signal generator
64, 64A time-series signal processor
65A area generator
66A area quality determination unit
100, 100A speckle measurement apparatus

The invention claimed is:

1. A speckle measurement apparatus, comprising:
an imager that captures scattered light images returned from an object to be measured when the object to be measured is irradiated with coherent light as speckle images; and
a controller that determines a measurement area that is a same site of the object to be measured in a plurality of the speckle images captured continuously in time series by the imager by incorporating a displacement amount of a relative positional relationship between the object to be measured and the imager,
wherein the controller is configured to compare the plurality of speckle images captured continuously in time series by the imager, detect the displacement amount of the relative positional relationship between the object to be measured and the imager, and determine the measurement area that is the same site of the object to be measured in the plurality of speckle images according to the detected displacement amount.

2. A speckle measurement apparatus, comprising:
an imager that captures scattered light images returned from an object to be measured when the object to be measured is irradiated with coherent light as speckle images; and
a controller that determines a measurement area that is a same site of the object to be measured in a plurality of the speckle images captured continuously in time series by the imager by incorporating a displacement amount of a relative positional relationship between the object to be measured and the imager,
wherein the controller is configured to divide a coordinate space of a speckle image captured by the imager into a plurality of divided areas each having a predetermined size, determine the divided area having least area-specific noise components as the measurement area, retrieve an area with a highest coincidence with the speckle image of the measurement area from a speckle image at next time, and regard the retrieved area as the measurement area at the next time.

3. The speckle measurement apparatus according to claim 2, wherein
the controller is configured to determine an image signal that is not linearly changed with respect to a change of a coherent light intensity as a local noise.

4. The speckle measurement apparatus according to claim 3, wherein the controller is configured to exclude the divided area where any of an average value, a maximum value, and a median of a contrast difference of brightness of all existing speckles is a threshold value or less from the measurement area.

5. A speckle measurement method, comprising:

irradiating an object to be measured with coherent light;

capturing scattered light images returned from the object to be measured as speckle images; and determining by a controller a measurement area that is a same site of the object to be measured in a plurality of the speckle images captured continuously in time series by incorporating a displacement amount of a relative positional relationship between the object to be measured and an imager, wherein the controller is configured to compare the plurality of speckle images captured continuously in time series by the imager, detect the displacement amount of the relative positional relationship between the object to be measured and the imager, and determine the measurement area that is the same site of the object to be measured in the plurality of speckle images according to the detected displacement amount.

* * * * *